United States Patent [19]

ElSohly

[11] Patent Number: 5,508,037
[45] Date of Patent: *Apr. 16, 1996

[54] STABLE SUPPOSITORY FORMULATIONS EFFECTING BIOAVAILABILITY OF $\Delta^9$-THC

[75] Inventor: Mahmoud A. ElSohly, Oxford, Miss.

[73] Assignee: The University of Mississippi, University, Miss.

[*] Notice: The term of this patent shall not extend beyond the expiration date of Pat. No. 4,933,363.

[21] Appl. No.: 382,500

[22] Filed: Feb. 2, 1995

Related U.S. Application Data

[62] Division of Ser. No. 65,117, May 21, 1993, Pat. No. 5,389,375.

[51] Int. Cl.$^6$ ............... A61K 9/02; A61K 47/44
[52] U.S. Cl. .................. 424/436; 424/DIG. 15; 514/786; 514/966
[58] Field of Search ........... 424/436, DIG. 15; 514/966, 786

[56] References Cited

U.S. PATENT DOCUMENTS 3,728,360  4/1973  Pars et al. ............... 549/390
4,933,363  6/1990  ElSohy ................. 514/454

Primary Examiner—Carlos A. Azpuru
Attorney, Agent, or Firm—Morgan & Finnegan

[57] ABSTRACT

Suppository formulations having long-term stability and containing readily bioavailable $\Delta^9$-THC derivatives.

17 Claims, No Drawings

STABLE SUPPOSITORY FORMULATIONS EFFECTING BIOAVAILABILITY OF Δ⁹-THC

This is a divisional of co-pending application Ser. No. 08/065, 117 filed May 21, 1993, now going to issue as U.S. Pat. No. 5,389,375.

FIELD OF THE INVENTION

The present invention relates to suppository formulations containing readily bioavailable $\Delta^9$-tetrahydrocannabinol derivatives wherein the suppositories have long-term stability.

BACKGROUND OF THE INVENTION

Delta-9-tetrahydrocannabinol ($\Delta^9$-THC) is the active ingredient of the plant Cannabis sativa (marijuana) which is responsible for the majority of the pharmacological effects of the plant. Many of the pharmacologic properties of the marijuana plant or $\Delta^9$-THC could be directed to specific therapeutic effects given the appropriate dosage form. Therapeutic activities associated with marijuana use or administration of $\Delta^9$-THC include, but are not limited to, antiemetic activity as disclosed in Sallan, S. E.; Zinberg, N. E.; and Frei, E., III. Antiemetic effect of delta-9-tetrahydrocannabinol in patients receiving cancer chemotherapy. *N. Engl. J. Med.*, 293:795–797, 1975; Sallan, S. E.; Cronin, C.; Zelen, M.; and Zinberg, N. E. Antiemetics in patients receiving chemotherapy for cancer. *N. Engl. J. Med.*, 302:135–138, 1980; Ungerleider, J. T.; Fairbanks, L. A.; and Andrysiak, T. THC or compazine for cancer chemotherapy patient—the USLA Study, Part II: Patient drug preference. *Am. J. Clin. Oncol.*, 8:142–147, 1985; and Regelson, W.; Butler, J. R.; Schultz, J.; Kirk, T.; Peek, L.: Green, M. L.; and Zalis, M. O. *The Pharmacology of Marihuana*, Vol. 2, Eds. M. C. Braude and S. Szara, Raven Press, N.Y., 1976, pp. 763–776, Analgesic activity is disclosed in Maurer, M.; Henn, V.; Dittrich, A.; and Hofmann, A. Delta-9-tetrahydrocannabinol shows antispastic and analgesic effects in a single case double-blind trial. *Eur. Arch. Psychiatry Clin. Neurosci.*, 240(1):1–4, 1990; Noyes, R.; Brunk, S. F; Avery, D. H.; and Canter, A. Psychologic effects of oral delta-9-tetrahydrocannabinol in advanced cancer patients. *Compr. Psychiat.*, 17(5):641–646, 1976; and Regelson et al. ibid.

Anti-spasticity is discussed in Maurer et al. ibid.

Appetite stimulation is noted by Maurer et al. and Noyes et al. ibid and Gagnon, M. A. and Eli, R. Les effets de la marijuana et de la d-amphetamine sur l'appetit, la consommation alimentire et quelques variables cardio-respiratoires chez l'homme (Effects of marihuana and of d-amphetamine on appetite, food intake, and some cardio-respiratory variables in man). *Union Med. Can.*, 104(6):914–921, 1975; Foltin, R. W.; and Fischmann, M. W. Behavioral analysis of marijuana effects on food intake in humans. *Pharmacol. Biochem. Behav.*, 30(2):551, 1988; Foltin, R. W.; Brady, J. V.; and Fischman, M. W. Behavioral analysis of marijuana effects on food intake in humans. *Pharmacol. Biochem. Behav.*, 25(3), 557–582, 1986; Bruera, E. Current pharmacological management of anorexia in cancer patients. *Oncologly*, Williston Park, 6(1), 125–130, 1992).

Antidepressant activity is discussed in Regelson et al and Maurer et al, ibid.

Treatment and prevention of migraine headache is discussed by El-Mallakh, R. S. Marihuana and migraine. *Headache*, 27(8):442–443, 1987; and Volfe, Z.; Dvilansky, A.; and Nathan, I. Cannabinoids block release of serotonin from platelets induced by plasma from migraine patients. *Int. J. Clin. Pharmacol. Res.*, 5(4):243–246, 1985.

Anti-anxiety is disclosed by McLendon, D. M.; Harris, R. T.; and Maule, W. F. Suppression of the cardiac conditioned response by delta-9-tetrahydrocannabinol: A comparison with other drugs. *Psychopharmacology*, 50(2):159–163, 1976; and Musty, R. E. Possible anxiolytic effects of cannabidiol. The *Cannabinoids: Chemical, Pharmacologic, and Therapeutic aspects*, Eds. S. Agurell, W. L. Dewey, and R. E. Willette, Academic Press, Orlando, Fla., 1984).

Treatment of glaucoma is the subject of Hepler, R. S.; Frank, I. M.; and Petrus R. Ocular effects of marihuana smoking. In: *The Pharmacology of Marihuana*, Eds. M. C. Braude and S. Szara, Raven Press, N.Y., 1976, pp. 815–824; El Solhy, M. A.; Harland, E.; and Waller, C. W. Cannabinoids in Glaucoma II: The effect of different cannabinoids on the intraocular pressure of the rabbit. *Curr. Eye Res.*, 3(6):841–850, 1984).

Improvement of night vision is taught by Reese, K. M. Cannahis seems to improve night vision of fisherman. *Chem. Eng. News.* 69(31):44, 1991; and West, M. E. Cannabis and night vision. Nature. 351(6329):703–704, 1991).

Formulation of $\Delta^9$-THC to be used as a medicinal agent has been problematic. Orally, $\Delta^9$-THC was found to be poorly absorbed (Ohlsson, A.: Lindgren, J. E.; Wahlen, A.; Agurell, S.; Hollister, L. E.; Gillespie, B. A. Plasma delta-9-tetrahydrocannabinol concentrations and clinical effects after oral and intravenous administration and smoking. *Clin. Pharmacol. Ther.* 28:409–416, 1980) with erratic bioavailability which is dependent on food intake (Pryor, G. T.; Husain, S.; Mitoma, C. Influence of fasting on the absorption and effects of delta-9-THC after oral administration of sesame oil. *Pharmacol. Biochem Behav.*, 6:331,341, 1976). From suppository formulations (both lipophilic and hydrophilic) there was no absorption of $\Delta^9$-THC (Perlin, E.; Smith C. G.; Nichols, A. I.; Almirez, R.; Flora, K. P.; Craddock, J. C.; and Peck, C. C. Disposition and bioavailability of various formulations of tetrahydrocannabinol in the Rhesus monkey. *J. Pharm. Sci.*, 74:171–174, 1985). The only formulation resulting in good bioavailability was an intramuscular injectable (Perlin et al. ibid) where $\Delta^9$-THC was formulated in Tween 80 (39 ± 13% bioavailability) or Emulphor-El 620 (102 ± 15% bioavailability). Injectibles are fraught with the problems of being invasive and requiring professional assistance (phlebotomist), and therefore in many cases preclude self medication.

In 1991 El Sohly et al. (El Sohly, M. A.; Stanford, D. F.; Harland, E. C.; Hikal, A. H.; Walker, L. A.; Little, T. L., Jr.; Rider, J. N.; and Jones, A. B. Rectal bioavailability of $\Delta^9$-tetrahydrocannabinol from the hemisuccinate ester in monkeys. *J. Pharm. Sci.*, 80(10):942–945, 1991.

El Sohly, M. A.; Little, T. L., Jr.; Hikal, A. H.; Harland, E.; Stanford, D. F.; and Walker, L. Rectal bioavailability of delta-9-tetrahydrocannabinol from various esters. *Pharmacol. Biochem. Behav.*, 40:497–502, 1991) reported on the development of a suppository formulation containing the hemisuccinate ester of $\Delta^9$-THC as a prodrug. This formulation resulted in high consistent bioavailability of $\Delta^9$-THC. Although the prodrug $\Delta^9$-THC-hemisuccinate was reasonably stable in the lipophilic base used for the suppository formulation, the stability was not enough to provide the shelf life required for the product to be marketed. It was therefore necessary to develop a formulation which would provide the required stability and shelf life.

It is an object of the present invention to provide a suppository formulation containing at least one bioavailable $\Delta^9$-THC derivative in which the suppository has long term stability and shelf life.

SUMMARY OF THE INVENTION

This invention is directed to a suppository formulation having long term stability and which contains $\Delta^9$-THC derivatives, such as $\Delta^9$-THC-hemisuccinate. The $\Delta^9$-THC derivatives are prodrugs for $\Delta^9$-THC.

DETAILED DESCRIPTION OF THE INVENTION

The present invention relates to suppository formulations containing a therapeutically effective amount of at least one $\Delta^9$-THC ester prodrug derivative represented by the formula:

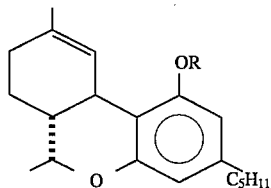

wherein R is an acyl group having a polar side chain, preferably R represents

and R' is an alkyl containing a carboxyl or amino group and having from 3 to 10 carbon atoms. In a preferred embodiment of the invention R is the hemisuccinic acid ester. Other useful polar esters are the hemi-ester of malonic acid and the alaninate ester of alanine. It has been found that salts of the terminal carboxylic acid group of the ester, for example, the N-methyl glutamine salt as well as the sodium and potassium salts are also useful.

The compounds are disclosed and described in U.S. Pat. No. 4,933,368. The disclosure of the '368 patent as well as the disclosures of all references which are recited in the present specification are expressly incorporated herein by reference thereto. These compounds are hydrolyzed in the blood stream releasing $\Delta^9$-THC to provide a high degree of bioavailability of $\Delta^9$-THC without regard to patient conditions and anomalies.

The present suppository formulations comprise a therapeutically effective amount of at least one $\Delta^9$-THC prodrug ester derivative and a pharmaceutically acceptable suppository base composition wherein the suppository base composition is such that the suppository formulation has long term stability. Specifically, the suppository base compositions useful in the present invention are such that any substantial amount of hydrolysis of the $\Delta^9$-THC prodrug ester derivative to free $\Delta^9$-THC prior to administration is substantially avoided.

Suppository formulations within the scope of the present invention are prepared by admixing a therapeutically effective amount of at least one $\Delta^9$-THC prodrug ester derivative with a suppository base which provides long term stability to the suppository formulation and the forming of the suppositories from the admixture by any recognized method of making suppositories. Such methods are well-known to those skilled in the art. The suppository base is one which allows the substantial avoidance of substantial amounts of hydrolysis of $\Delta^9$-THC prodrug derivative(s) contained in the suppository. Typically, such suppository bases are those which are lipophilic, more preferably, the suppository base is an aprotic lipophilic base such as a triglyceride lipophilic base or a paraffinic base comprising mixtures of hydrocarbons. The suppository base should have a melting temperature that ensures melting of the suppository within a reasonable time after insertion. Typically the suppository base can include mixtures of hydrocarbons (paraffins) having a melting point range of from about 32° to 36° C. or a triglyceride mixture of fatty acids having a melting point range of from about 32° to 36° C. The mixture of hydrocarbons can preferably be a mixture of hard paraffin (about 50–60%) and liquid paraffin (about 40–50%) having a melting point range of about 32° to 36° C. A particularly preferred triglyceride base is one of the Wecobee products, most preferably, Wecobee W.

The $\Delta^9$-THC prodrug ester derivatives are administered in the suppository formulation in non-toxic dosage concentrations sufficient to insure the release of sufficient dosage units of $\Delta^9$-THC into the blood to provide the desired therapeutic effect. Specifically, the dosage amount contained in the suppository of $\Delta^9$-THC prodrug ester derivative is that amount needed to provide: (1) the desired anti-emetic effect; the desired analgesic effect or pain or spasticity alleviating effect; the desired appetite stimulating effect; the desired antidepression effect; the desired anti-anxiety effect; the desired treatment or prevention of migraine headaches; the desired lowering of intraocular pressure in patients being treated for glaucoma; or the desired improvement in night vision. The actual dosage amount administered can be determined by physical and physiological factors such as body weight, severity of condition, and idiopathy of the patient. With these considerations in mind, the dosage of releasable $\Delta^9$-THC for a particular subject and or course of treatment can readily be determined.

The following examples are presented as specific and preferred embodiments. Although the invention has been described in conjunction with specific embodiments, it is evident that many alternatives and variations will be apparent to those skilled in the art. Accordingly, the present invention is intended to embrace all alternatives and variations that fall within the spirit and scope of the appended claims. All references and citations mentioned in this disclosure are hereby incorporated by reference.

EXAMPLE I $\Delta^9$-THC-hemisuccinate (Dronabinol hemisuccinate) was formulated into four suppository bases, namely, Wecobee W (Stephan Company, Maywood, N.J.), Witepsol H15 (Huls Petrarch Systems, Bristol, Pa.), Hydrokote (Capital City Products Company, Columbus, Ohio), and paraffin 45/55 (a mixture of liquid paraffin and hard paraffin in a ratio of 45:55 which provided a melting range of 32°–36° C.) at a concentration of 6.59 mg/suppository (equivalent to 5 mg $\Delta^9$-THC per suppository). Each base was added to a specified amount of $\Delta^9$-THC-hemisuccinate in a crucible in the proper ratio with each suppository weighing an average of 1.92 grams. The mixture was then melted together over a hot water bath at approximately 70° C. After all the base was melted and mixed well with the drug, the mixture was allowed to cool with continuous mixing. When the base just began to re-solidify, it was poured into prelubricated suppository molds. The suppositories were allowed to solidify in the mold for at least one hour at room temperature. The excess base was then scraped off the mold, the mold opened, and the suppositories retrieved.

The suppositories made with each of the four bases were then evenly divided into three groups. One group from each base was stored at room temperature, one group at 4° C. (refrigerated), and the third group was stored at an elevated temperature (34° C. in a constant temperature oven).

Samples of the suppositories from each base were analyzed at time zero to establish the actual concentration prior to storage. The analysis of each of the four suppository bases for $\Delta^9$-THC and $\Delta^9$-THC-hemisuccinate was carried out by HPLC using the following general procedure applicable to lipophilic bases:

| Analysis of Different Lipophilic Suppository Bases for $\Delta^9$-THC and Its Hemisuccinate Ester | |
|---|---|
| Solvent delivery system: | Waters Model 6000 Pump connected to a U6K Injector. |
| Column: | Waters μ BondaPak $C_{18}$, 3.9 mm × 30 cm, 10 μm particle size. |
| Solvent: | Methanol/water/acetic acid (80:20:0.01) filtered through 0.45 μ nylon filter used at 1.2 mL/min. |
| Detector: | Variable wave length detector (Hitachi 100-40 with Altex 155-00 flow cell) operated at 214 nm. Peaks were integrated using an HP Model 3394A Integrator. |
| Internal Standard: | $\Delta^9$-THC-Hemiglutarate was used as internal standard and was added in the extraction solvent (methanol) at a concentration of 0.5 mg/mL. |

Extraction of $\Delta^9$-THC and $\Delta^9$-THC-Hemisuccinate From the Suppository Base The entire suppository was melted and a sample of the melted suppository was transferred to a pre-weighed 12×75 nun test tube (approximately 200 mg for suppositories containing the equivalent of 5 mg $\Delta^9$-THC and approximately 100 mg for suppositories containing the equivalent of 10 mg $\Delta^9$-THC). After the material was allowed to return to room temperature, the weight of the suppository sample was accurately determined.

To the test tube containing the suppository sample was then added 1 mL of the internal standard solution (0.5 mg/mL $\Delta^9$-THC-hemiglutarate in methanol). The tube was then inserted into a heating block at 50° C. for 1 min followed by vortexing while hot (keep base melted) for 30 sec. The tube was then capped and transferred to a refrigerator to solidify the base. The methanolic extract was then filtered through a cotton plug into a GC vial. An aliquot (15 μL) of the extract was then injected into the HPLC system. The peak areas for $\Delta^9$-THC, $\Delta^9$-THC-hemisuccinate, and the internal standard were measured. The peak area ratios of $\Delta^9$-THC/I.S. and $\Delta^9$-THC-hemisuccinate/I.S. were then calculated. Using calibration curves for $\Delta^9$-THC and $\Delta^9$-THC-hemisuccinate, prepared for each suppository base, the concentration of these analytes were determined.

Preparation of Calibration Curves for $\Delta^9$-THC and $\Delta^9$-THC-Hemisuccinate The calibration curves were prepared by spiking 200 mg samples of the base with various amounts of $\Delta^9$-THC and $\Delta^9$-THC-hemisuccinate followed by extraction of the spiked samples according to the same procedure outlined above. The following concentrations of $\Delta^9$-THC were used: 0, 125, 250, 375, and 500 μg/g base, and the following concentrations of $\Delta^9$-THC-hemisuccinate were used: 0, 1.5, 2.5, 3, and 3.75 mg/g base.

Following the time zero analysis, the suppositories were stored at the different temperatures (room temperature, refrigeration, and 34° C.) for twelve months and were then reanalyzed in the same way. The results of the one-year analyses are shown in Table 1.

The data show that storage of suppositories at room temperature or elevated temperature (34° C.) resulted in severe degradation of the hemisuccinate ester formulated in Witepsol H15 with moderate loss at 4° C. (21% loss). Of the other three bases, only Wecobee retained > 90% of the original concentration of the hemisuccinate at both 4° C. and at room temperature. Paraffin base showed no degradation at 4° C.

EXAMPLE II $\Delta^9$-THC-hemisuccinate was formulated in the same bases as described under Example I. The suppositories were analyzed at time zero and then stored refrigerated (4° C.). Samples from each group (base) were removed periodically for analysis over a period of twenty-one months. The results of the periodic analysis are shown in Table 2.

The data show the gradual degradation of the THC-hemisuccinate takes place when formulated in Hydrokote and Witepsol H15 and is more severe in the latter. On the other hand, both Wecobee and paraffin bases retain 95% or more of the original concentration of the drug up to twenty-one months. Examination of the HPLC chromatograms shows that the only degradation product is $\Delta^9$-THC itself, indicating that hydrolysis of the hemisuccinate ester is the cause of degradation.

EXAMPLE III $\Delta^9$-THC-hemisuccinate was formulated in different lipophilic suppository bases in the same manner as described under Example I. The bases used in this example were as follows: Witepsol H15, Witepsol H15 with 0.25% butyric acid, Witepsol H15 with the drug introduced in paraffin oil, Witepsol H15 with 5% corn starch; Hydrokote, and Hydrokote with 0.25% butyric acid. The suppositories were analyzed at time zero and then stored refrigerated (4° C.) with periodic analysis over a six-month period. The results of the analyses are shown in Table 3. The data show that the modifications made with Witepsol H15 and Hydrokote did not significantly enhance the stability of $\Delta^9$-THC-hemisuccinate. In all cases, less than 90% of the starting material was recovered after six months.

This example demonstrates that the source of instability does not lie in the possible hydroscopic nature of the suppository base. The addition of materials to help prevent any water drawn from the air to hydrolyze the ester did not enhance the stability of the ester.

EXAMPLE IV $\Delta^9$-THC-hemisuccinate was formulated in Witepsol H15, Hydrokote, Kaomel, and Suppocire lipophilic bases in the same fashion as described under Example I, except that the concentration of the drug in the suppositories was doubled (13.18 mg/suppository equivalent to 10 mg a $\Delta^9$-THC/suppository). Each group of suppositories from each base was analyzed at time zero. The suppositories were then stored refrigerated (4° C.) for eighteen months followed by reanalysis using the same procedure outlined under Example I. The results of the analysis are summarized in Table 4. The data show that extensive degradation occurred in all bases over the eighteen-month period.

EXAMPLE V $\Delta^9$-THC-hemisuccinate was formulated in two hydrophilic suppository bases, namely polyethylene glycol 600/3350 and Tween 61/glycerolmonolaurate in the same manner as described under Example I, except that the concentration of the drug was the equivalent of 10 mg $\Delta^9$-THC/suppository (13.18 mg $\Delta^9$-THC-hemisuccinate/suppository). The suppositories were analyzed at time zero following the procedure outlined under Example I, with the following exceptions:

1. The internal standard was octanophenone at a concentration of 0.2 mg/mL in iso-octane.

2. The extraction process was as follows: A sample of the suppository was accurately weighed in a 12× 75 mm test tube. The tube was then added 1 mL of distilled water and 1 mL of the internal standard solution and the mixture vortexed until all the base was totally partitioned between the two solvents. The iso-octane layer (top) was then transferred to another tube and the solvent evaporated. The residue was then dissolved in 1 mL methanol, and 15 μL of the final solution was injected into the HPLC. Peak area measurements and concentration calculations were performed as above.

The suppositories were then stored refrigerated and analyzed after three weeks, six weeks, and four months of storage. The results of the analysis are summarized in Table 5. The data show that $\Delta^9$-THC-hemisuccinate is extremely unstable in hydrophilic bases.

TABLE 1

Stability of $\Delta^9$-THC-hemisuccinate in different lipophilic suppository bases following storage for one year at different temperatures
Percent $\Delta^9$-THC-Hemisuccinate Remaining After One-Year Storage

| Temperature | Wecobee W | Paraffin | Hydrokote | Witepsol H15 |
|---|---|---|---|---|
| 4° C. | 98 | 100 | 85 | 79 |
| 20° C. (RT) | 98 | 87 | 87 | 33 |
| 34° C. | 81 | 82 | 85 | 26 |

TABLE 2

Stability of $\Delta^9$-THC-Hemisuccinate in Different Lipophilic Suppository Bases Following Storage Over a Period of Twenty-One Months at 4° C.
Percent $\Delta^9$-THC-Hemisuccinate Remaining After Twenty-One Months Storage

| Time | Wecobee W | Paraffin Base | Hydrokote | Witepsol H15 |
|---|---|---|---|---|
| 3 Months | 96 | 99 | 91 | 88 |
| 6 Months | 99 | 95 | 84 | 78 |
| 12 Months | 98 | 100 | 85 | 79 |
| 21 Months | 95 | 98 | 77 | 65 |

TABLE 3

Percent of $\Delta^9$-THC-Hemisuccinate in Various Lipophilic Suppository Formulations After Refrigerated Storage (4° C.) Over a Six-Month Period
Percent $\Delta^9$-THC-Hemisuccinate After Sixth Months Storage

| Time | Witepsol | Witepsol/ Butyric Acid | Witepsol/ Corn Starch | Witepsol/ Paraffin Oil | Hydrokote | Hydrokote/ Butyric Acid |
|---|---|---|---|---|---|---|
| 0 | 97 | 97 | 99 | 97 | 99 | 99 |
| 2 Mos | 89 | 92 | 95 | 90 | 92 | 94 |
| 3 Mos | 88 | 91 | 92 | 89 | 91 | 93 |
| 6 Mos | 78 | 83 | 86 | 75 | 84 | 84 |

TABLE 4

Percent of $\Delta^9$-THC-Hemisuccinate Remaining Following Refrigerated Storage (4° C.) in Various Lipophilic Suppository Bases Over a Period of Eighteen Months

| Base | $\Delta^9$-THC-Hemisuccinate Remaining After Months Storage |
|---|---|
| Witepsol H15 | 63.0% |
| Hydrokote | 71.3% |
| Kaomel | 37.2% |
| Suppocire | 59.2% |

TABLE 5

Percent of $\Delta^9$-THC-Hemisuccinate Remaining Following Refrigerated Storage (4° C.) in Two Hydrophilic Suppository Bases
Percent of $\Delta^9$-THC-Hemisuccinate Remaining

| Time After Preparation | Polyethyleneglycol 600/3350 | Tween 61/ Glycerylmonolaurate |
|---|---|---|
| 3 Weeks[1] | 56% | 0% |
| 6 Weeks | 38% | N/A |
| 4 Months | 11% | N/A |

[1]The instability of the hemisuccinate of $\Delta^9$-THC in hydrophilic bases was evident from time of preparation. Analysis of the suppositories immediately after preparation showed 65% of nominal concentration in PEG 600/3350 and complete hydrolysis of Tween 61/glycerylmonolaurate base.

I claim:

1. A method of providing a therapeutic effect for those in needed thereof by providing a non-toxic dosage concentration sufficient to insure release of sufficient dosage to provide the desired therapeutic effect said method comprising rectally administering a long term stable suppository formulation comprising a therapeutically effective amount of at least one $\Delta^9$-THC prodrug ester having the formula:

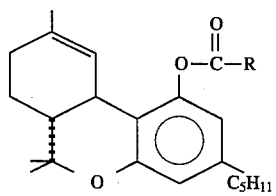

where R is an alkyl containing a carboxyl or amino functional group in a pharmaceutically acceptable rectal suppository base wherein the suppository base affords long term stability of the $\Delta^9$-THC prodrug ester contained in the suppository formulation.

2. The method of claim 1, wherein the producing ester is the hemiester of succinic acid, the hemiester of malonic acid or the alaninate ester of alanine.

3. The method of claim 1, wherein the suppository base is a lipophilic suppository base.

4. The method of claim 1, wherein the suppository base is an aprotic lipophilic suppository base.

5. The method of claim 1, wherein the suppository base is a mixture of hydrocarbons (paraffins) or a triglyceride mixture of fatty acids.

6. The method of claim 5, wherein the melting range of the suppository base is about 32° to 36° C.

7. The method of claim 5, wherein the suppository base is a triglyceride mixture.

8. The method of claim 5, wherein the base is a mixture of about 50–60% hard paraffin and 40–50% liquid paraffin.

9. The method of claim 7, where the producing ester is the hemiester of succinic acid.

10. A method of claim 8, wherein the producing ester is the hemiester of succinic acid.

11. The method of claim 1, wherein the suppository base affords long term stability of the $\Delta^9$-THC prodrug ester contained in the suppository formulation such that greater than 90% of the original concentration of the ester is retained for at least one year.

12. A method according to claim 1, wherein the desired therapeutic effect is of inducing analgesia and alleviating pain and spasticity.

13. A method according to claim 1, wherein the desired therapeutic effect is of appetite stimulation.

14. A method according to claim 1, wherein the desired therapeutic effect is of treating depression.

15. A method according to claim 1, wherein the desired therapeutic effect is of treating anxiety.

16. A method according to claim 1, wherein the desired therapeutic effect is of treating and preventing migraine headaches.

17. A method according to claim 1, wherein the desired therapeutic effect is of improving night vision.

* * * * *

UNITED STATES PATENT AND TRADEMARK OFFICE
CERTIFICATE OF CORRECTION

PATENT NO. : 5,508,037
DATED : April 16, 1996
INVENTOR(S) : Mahmoud A. ElSohly

It is certified that error appears in the above-indentified patent and that said Letters Patent is hereby corrected as shown below:

Col. 9: Claim 2, line 1, delete "producing" and insert therefor -- prodrug --.

Col. 10: Claim 9, line 1, delete "producing" and insert therefor -- prodrug --.

Claim 10, line 1, delete "producing" and insert therefor -- prodrug --.

Signed and Sealed this

Sixteenth Day of July, 1996

Attest:

BRUCE LEHMAN

*Attesting Officer*   *Commissioner of Patents and Trademarks*